(12) United States Patent
Sasaki et al.

(10) Patent No.: US 6,392,048 B1
(45) Date of Patent: May 21, 2002

(54) PROCESS FOR PREPARING CARBOCYCLIC OR HETEROCYCLIC NITRILES BY VAPOR PHASE AMMOXIDATION

(75) Inventors: Yutaka Sasaki; Hiroshi Utsumi; Akimitsu Morii; Kazuo Morishita, all of Yokohama (JP)

(73) Assignee: Mitsubishi Rayon Co., Ltd., Tokyo-to (JP)

( * ) Notice: Subject to any disclaimer, the term of this patent is extended or adjusted under 35 U.S.C. 154(b) by 0 days.

(21) Appl. No.: 09/629,418

(22) Filed: Jul. 31, 2000

Related U.S. Application Data

(62) Division of application No. 08/951,463, filed on Oct. 16, 1997, now Pat. No. 6,187,943.

(30) Foreign Application Priority Data

Oct. 24, 1996  (JP) ............................................. 8-299262
Oct. 24, 1996  (JP) ............................................. 8-299263

(51) Int. Cl.$^7$ .................... C07D 215/00; C07D 221/02; C07D 231/00; C07D 211/00; C07D 231/10
(52) U.S. Cl. ......................... 546/287; 546/26; 546/112; 546/152; 548/356.1; 548/373.1; 549/29; 549/61
(58) Field of Search ................................ 546/287, 152, 546/112, 252; 548/356.1, 373.1; 549/29, 61

(56) References Cited

U.S. PATENT DOCUMENTS

| | | | |
|---|---|---|---|
| 3,427,343 A | 2/1969 | Callahan et al. | 260/465.3 |
| 3,927,007 A | 12/1975 | Lussling et al. | 260/294.9 |

(List continued on next page.)

FOREIGN PATENT DOCUMENTS

| | | | |
|---|---|---|---|
| EP | 767165 | 9/1996 | C07C/253/28 |
| EP | 750942 | 1/1997 | B01J/35/02 |

OTHER PUBLICATIONS

Mitsubishi Gas Chemical Co., Inc., "MGC–Badger Isophthalonitrile Process", Process Handbook, vol. 2, IPN–MGC–(76/4)B, Edited by Petroleum Society of Japan, 1976, pp. 1–2.

"A new development into catalytic reactions", Modern Chemical Engineering: Fluidized Bed Engineering, pp. 97–104, 1981.

"Ammoxidation of propylene", Fluidized Bed Reactors, pp. 190–193, Edited by the Society of Chemical Engineers, 1987.

(List continued on next page.)

*Primary Examiner*—Sabiha Qazi
(74) *Attorney, Agent, or Firm*—Wenderoth, Lind & Ponack, L.L.P.

(57) ABSTRACT

The present invention provides a process for preparing carbocyclic or heterocyclic nitrites by the vapor phase contact ammoxidation of carbocyclic compounds or heterocyclic compounds, in which the reaction is carried out effectively without the increase of the amount of ammonia or oxygen used or the introduction of steam to give the nitrites as the objective products stably with the passage of time in a high yield with a high selectivity.

A process for preparing carbocyclic or heterocyclic nitrites comprising subjecting the corresponding starting carbocyclic or heterocyclic compounds to ammoxidation via the vapor phase catalytic reaction in a fluidized bed reactor, in which the reaction is carried out in the presence of a metal oxide fluidized bed catalyst containing vanadium and/or molybdenum as the catalyst, oxygen-containing gas being supplied through an oxygen-containing gas inlet provided at the bottom of the fluidized bed reactor, the starting cyclic compound and ammonia being supplied at a level higher than the oxygen-containing gas inlet, a fluidized bed being formed so that the ratio of the amount of catalyst (Wb) fluidized at a level higher than the inlet of the starting cyclic compound to the amount of catalyst (Wa) fluidized at a level higher than the oxygen-containing gas inlet in the reaction zone is in the range of Wb/Wa=0.01–0.95 by weight.

5 Claims, 1 Drawing Sheet

U.S. PATENT DOCUMENTS

| | | | |
|---|---|---|---|
| 3,959,297 A | 5/1976 | Ishioka et al. | 260/294.9 |
| 3,959,339 A | 5/1976 | Saito et al. | 260/465 C |
| 4,070,393 A | 1/1978 | Angstadt et al. | 260/465 C |
| 4,336,205 A | 6/1982 | Onishi et al. | 260/465 |
| 4,447,612 A | 5/1984 | Beschke et al. | 546/285 |
| 4,590,011 A | 5/1986 | Sasaki et al. | 502/20 |
| 4,618,593 A | 10/1986 | Sasaki et al. | 502/20 |
| 4,709,071 A | 11/1987 | Sasaki et al. | 558/322 |
| 4,868,330 A * | 9/1989 | Ramachanran et al. | 558/320 |
| 4,963,687 A | 10/1990 | Saito et al. | 546/286 |
| 4,985,581 A | 1/1991 | Saito et al. | 558/327 |
| 5,059,573 A | 10/1991 | Sasaki et al. | 502/205 |
| 5,070,059 A | 12/1991 | Saito et al. | 502/206 |
| 5,808,143 A * | 9/1998 | Karrer et al. | 562/407 |
| 6,083,869 A * | 7/2000 | Albonetti et al. | 502/325 |
| 6,187,943 B1 * | 2/2001 | Sasaki et al. | 558/318 |

OTHER PUBLICATIONS

"Aromatic nitriles" and "Aromatic ammoxidation reaction", Practical Catalysts Classified By The Reactions To Which They Are Applied, pp. 372–379, Published by Chemical Industry Publisher, 1970.

* cited by examiner

PROCESS FOR PREPARING CARBOCYCLIC OR HETEROCYCLIC NITRILES BY VAPOR PHASE AMMOXIDATION

This application is a divisional application of Ser. No. 08/951,463, filed Oct. 16, 1997, now U.S. Pat. No. 6,187,943 B1, issued on Feb. 13, 2001.

BACKGROUND OF THE INVENTION

1. Field of the Invention

The present invention relates to a process for preparing carbocyclic or heterocyclic nitriles. Particularly, the present invention relates to a process for preparing carbocyclic or heterocyclic nitriles comprising subjecting a carbocyclic or heterocyclic compound to ammoxidation via vapor phase catalytic fluidized bed reaction. The carbocyclic or heterocyclic nitrites are useful as intermediates for a variety of pharmaceutical or agricultural chemicals, functional chemicals, polymers, and the like.

2. Background Art

As the process for preparing these nitrites are known a variety of methods, among which a method comprising the ammoxidation of carbocyclic or heterocyclic compounds has also been proposed as one of the important methods.

A variety of methods have been proposed for preparing carbocyclic nitrites via the vapor phase ammoxidation. Thus, Japanese Patent Laid-Open Publication No. 13141/1974 (U.S. Pat. No. 3,803,204) discloses a method comprising ammoxidation of xylene or toluene in the presence of a Mo catalyst, and Japanese Patent Laid-Open Publication No. 90238/1978 (U.S. Pat. No. 4,124,631) discloses a method comprising ammoxidation of methyl-substituted aromatic compounds in the presence of a V-P catalyst. Also, Japanese Patent Laid-Open Publication Nos. 13944/1981 (U.S. Pat. No. 4,336,205) and 120351/1987 (U.S. Pat. No. 4,814,479) disclose an ammoxidation method of alkyl aromatic compounds in the presence of a V-Sb catalyst; Japanese Patent Laid-Open Publication No. 10753/1988 discloses an ammoxidation method in the presence of a Sb—Sn catalyst; Japanese Patent Laid-Open Publication No. 63563/1989 (U.S. Pat. No. 4,939,260) in the presence of a Ti- and Si and/or Zr-containing catalyst; and Japanese Patent Laid-Open Publication No. 170724/1993 (EP 525367) in the presence of a P—Mo/Si catalyst, respectively. Furthermore, Japanese Patent Laid-Open Publication No. 190646/1988 discloses an ammoxidation method of alkyl aromatic compounds or alkyl-substituted alicyclic compounds in the presence of a Fe—Sb catalyst.

A variety of methods have been proposed also for preparing heterocyclic nitrites via the vapor phase ammoxidation. Thus, Japanese Patent Publication Nos. 7511/1965, 13572/1970 and 34673/1974, Japanese Patent Laid-Open Publication No. 4556/1972 (U.S. Pat. No. 3,927,007), Japanese Patent Laid-Open Publication No. 41871/1975 (U.S. Pat. No. 4,001,255), Japanese Patent Laid-Open Publication No. 80864/1976 (U.S. Pat. No. 3,959,297), Japanese Patent Laid-Open Publication No. 17360/1980, Japanese Patent Laid-Open Publication No. 139444/1981 (U.S. Pat. No. 4,336,205), Japanese Patent Laid-Open Publication No. 156038/1982 (U.S. Pat. No. 4,447,612), Japanese Patent Laid-Open Publication No. 208575/1988, and Japanese Patent Laid-Open Publication No. 275564/1989 (U.S. Pat. No. 4,963,687) disclose methods of preparing cyanopyridines from alkyl-substituted pyridines; Japanese Patent Laid-Open Publication Nos. 30382/1974 and 145672/1980, Japanese Patent Laid-Open Publication No. 156039/1982 (U.S. Pat. No. 4,419,272, U.S. Pat. No. 4,496,729), and Japanese Patent Laid-Open Publication No. 81448/1996 (EP 698603) disclose methods of preparing cyanopyrazines from methylpyrazines; Japanese Patent Laid-Open Publication No. 111566/1977 (U.S. Pat. No. 4,055,514) discloses a method of preparing cyanothiazole from methylthiazole; Japanese Patent Laid-Open Publication No. 99360/1987 (U.S. Pat. No. 4,603,207) discloses a method of preparing cyanopyridine from methylpyridine and methylpiperidine; Japanese Patent Laid-Open Publication No. 10753/1988, Japanese Patent Laid-Open Publication No. 72675/1988 (U.S. Pat. No. 4,778,890), Japanese Patent Laid-Open Publication No. 152360/1989 (U.S. Pat. No. 4,778,890), Japanese Patent Laid-Open Publication No. 31730/1989 (U.S. Pat. No. 4,931,561), Japanese Patent Laid-Open Publication No. 31731/1989 (U.S. Pat. No. 4,931,561), Japanese Patent Laid-Open Publication No. 31769/1989 (U.S. Pat. No. 4,931,561), Japanese Patent Laid-Open Publication No. 63563/1989 (U.S. Pat. No. 4,939,260), Japanese Patent Laid-Open Publication No. 126548/1992 (U.S. Pat. No. 5,139,988), and Japanese Patent Laid-Open Publication No. 170724/1993 (EP 525367) disclose methods of ammoxidation of alkyl-substituted heterocyclic compounds to prepare nitriles; and Japanese Patent Laid-Open Publication No. 190646/1988 discloses a method of ammoxidation of alkyl-substituted heterocyclic compounds or alkyl-substituted alicyclic compounds, respectively, to prepare corresponding nitrites.

While giving high yields of carbocyclic or heterocyclic nitrites, these methods had many problems to be solved in the case of the commercial production, particularly in the case of the large scale production of these nitrites. That is, the synthetic reaction of nitrites by the vapor phase catalytic ammoxidation of carbocyclic compounds or heterocyclic compounds evolved a large amount of reaction heat, and thus there was a problem of local overheating in the large scale production of nitrites which led to the difficulty in controlling the reaction temperature and thus increased the formation of by-products resulting in the lowering of the yield of the nitriles as the desired products. There was also a problem of the lowering of the yield of the nitrites as the desired products with the passage of time due to the deposition of carbonaceous matter on the catalyst and due to the deterioration of the catalyst used through its reduction. Such phenomena become more distinguished as the supply gas has a higher concentration of the carbocyclic compound or heterocyclic compound as the starting material. Therefore, it would have been necessary to lower the concentration of these starting cyclic compounds in the industrial production of carbocyclic or heterocyclic nitriles via the vapor phase ammoxidation reaction. It was also required for eliminating the above described defects in some cases to increase the amounts of ammonia and oxygen used, to add steam in a large amount, or to take into account the introduction of an inert gas in order to remove the composition of the raw material gas from the explosion composition range.

As one of the methods for solving these problems, there may be mentioned the production via fluidized bed reaction. However, this method still had problems to be solved such as the substantial lowering of the yield of the objective product due to the lowering of the catalyst activity with it the passage of time in the ammoxidation reaction is a fluidized bed technology is simply applied as illustrated hereinafter in comparative examples. It is duly noted that it was recommended in Japanese Patent Laid-Open Publication No. 41871/1975 (U.S. Pat. No. 4,001,255), Japanese Patent Laid-Open Publication No. 275564/1989 (U.S. Pat. No.

4,963,687) and Japanese Patent Laid-Open Publication No. 170724/1993 (EP 525367) that the ammoxidation reaction of heterocyclic compounds should be carried out in a fluidized bed. However, there remained problems to be solved such as substantial lowering of the yield of the objective product due to decrease in the catalyst activity with the passage of time even when the ammoxidation reaction is carried out simply over a fluidized bed catalyst as illustrated hereinafter in comparative examples.

SUMMARY OF THE INVENTION

The present invention has been made for the purpose of solving the problems in the prior art described above, and the object of the present invention is to provide an economically advantageous process for preparing nitrites comprising subjecting carbocyclic compounds or heterocyclic compounds to ammoxidation via vapor phase catalytic fluidized bed reaction to prepare the corresponding nitriles, in which the reaction is carried out effectively without the necessity of increasing the amount of ammonia or oxygen used or the necessity of introduction of steam in a large amount to give the nitriles as the objective products stably with the passage of time in a high yield with a high selectivity.

The present inventors have now found that a method for supplying starting materials for the reaction can be successfully designed to suppress the accumulation of carbonaceous matters deposited on the catalyst and to suppress the deterioration of the catalyst due to reduction, so that the carbocyclic or heterocyclic nitriles as the objective products are obtained in high yields, thus having reached the present invention.

The present invention accordingly relates to a process for preparing nitrites comprising subjecting a carbocyclic compound or a heterocyclic compound to ammoxidation via vapor phase catalytic reaction in a fluidized bed reactor, in which the reaction is carried out in the presence of a vanadium- and/or molybdenum-containing metal oxide catalyst, oxygen-containing gas being supplied through an oxygen-containing gas inlet provided at the bottom of the fluidized bed reactor, a carbocyclic compound or a heterocyclic compound and ammonia being supplied at a level higher than the oxygen-containing gas inlet, a fluidized bed being formed so that the ratio of the amount of catalyst (Wb) fluidized at a level higher than the inlet of the carbocyclic compound or heterocyclic compound to the amount of catalyst (Wa) fluidized at a level higher than the oxygen-containing gas inlet in the reaction zone is in the range of Wb/Wa of 0.01 to 0.95 by weight.

Figure 1:
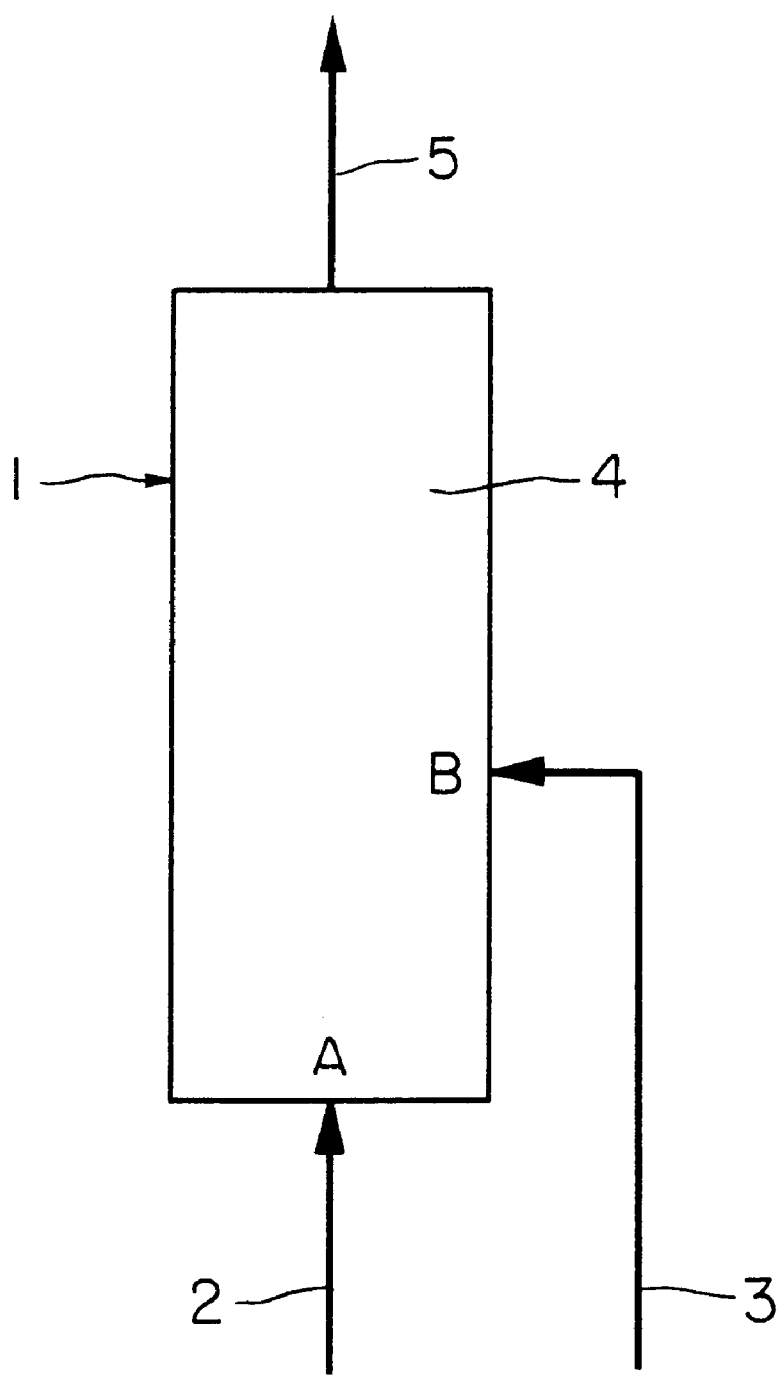
FIG. 1 is a schematic view illustrating a fluidized bed reactor used according to the present invention.

In the fluidized bed reactor of FIG. 1 is charged a catalyst. The oxygen-containing gas is supplied from the gas inlet A through the supply pathway 2, and the carbocyclic compound or heterocyclic compound and ammonia are supplied from the gas inlet B provided at a part higher than the gas inlet A through the supply pathway 3 to the fluidized bed reactor 1, respectively. The catalyst particles involved in the gas flow are separated from the gas flow in a cyclone separator at the top of the reactor and returned to the bottom part of the catalyst layer. The reaction gas having the catalyst particles separated therefrom is exhausted from the fluidized bed reactor 1.

1. a fluidized bed reactor,
2. a supply pathway of oxygen-containing gas,
3. a supply pathway of raw material cyclic compound-containing gas,
4. a reaction zone,
5. a reaction gas exhaust pathway,
A. an inlet for an oxygen-containing gas,
B. an inlet for a starting cyclic compound-containing gas.

DETAILED DESCRIPTION OF THE PREFERRED EMBODIMENTS

The present invention relates to the vapor phase catalytic fluidized bed reaction, more precisely to the reaction of a carbocyclic compound or heterocyclic compound (referred to hereinafter as a starting cyclic compound) with ammonia and oxygen, that is the ammoxidation reaction of a carbocyclic compound or heterocyclic compound.

The starting carbocyclic compound used in the present invention is, in one aspect, a carbocyclic compound which contains a carbocyclic ring selected preferably from the group consisting of benzene, naphthalene, antracene, phenanthrene, cyclohexadiene, cyclohexene, cyclohexane, dihydronaphthalene, tetraline and decaline, and contains as a side chain at the ring at least one selected preferably from the group consisting of a methyl group, an ethyl group, a propyl group, an isopropyl group, a formyl group, an acetyl group, a hydroxymethyl group, a hydroxyethyl group, a hydroxyisopropyl group, a methoxycarbonyl group, an ethoxycarbonyl group, a propoxycarbonyl group and an isopropoxycarbonyl group. The carbocyclic compound can also contain a substituent or substituents such as a halogen group, a hydroxyl group, an alkoxyl group, an amino group, a nitro group, a cyano group and a phenyl group.

Preferred examples of carbocyclic compounds include toluene, xylene, trimethylbenzene, ethylbenzene, isopropylbenzene, diisopropylbenzene, isopropyltoluene, methylnaphthalene, dimethylnaphthalene, ethylnaphthalene, methyltetraline, dimethyltetraline, chlorotoluene, dichlorotoluene, trichlorotoluene, bromotoluene, iodotoluene, methyl-aniline, dimethylaniline, cresol, tolunitrile, methylanisole, phenoxytoluene, and the like. These carbocyclic compounds may be used singly or in combination thereof.

The starting heterocyclic compound used in the present invention, in another aspect of the present invention, is a heterocyclic compound which contains a heterocyclic ring selected preferably from the group consisting of furan, pyrrole, indole, thiophene, pyrazole, imidazole, thiazole, oxazole, pyran, pyridine, quinoline, isoquinoline, pyrimidine, pyridazine, pyrazine, oxolane, pyrroline, pyrrolidine, thiolane, imidazoline, imidazolidine, oxane, piperidine and piperazine, and contains as a side chain at the ring at least one selected preferably from the group consisting of a methyl group, an ethyl group, a propyl group, an isopropyl group, a formyl group, an acetyl group, a hydroxymethyl group, a hydroxyethyl group, a hydroxyisopropyl group, a methoxycarbonyl group, an ethoxycarbonyl group, a propoxycarbonyl group and an isopropoxycarbonyl group. The carbocyclic compound can also contain a substituent or substituents such as a halogen group, a hydroxyl group, an alkoxyl group, an amino group, a nitro group, a cyano group and a phenyl group.

Preferred examples of heterocyclic compounds include furfural, methylthiophene, 3-methylthiophene, 2-formylthiophene, 4-methyl-thiazole, 2-methylpyridine, 3-methylpyridine, 4-methylpyridine, 2,3-dimethylpyridine, 2,4-dimethylpyridine, 2,5-dimethylpyridine, 2,6- dimethylpyridine, 3,4-dimethylpyridine, 3,5-dimethylpyridine, 2-methyl-5-ethylpyridine, 2,4,6-trimethylpyridine, 2-methylquinoline, 3-methylquinoline, 4-methylquinoline, 2-methylpyrazine, 2,5-dimethylpyrazine, 2-methylpiperidine, 3-methylpiperidine, 4-methylpiperidine, 2-methylpiperazine, and the like. These heterocyclic compounds may be used singly or in combination thereof.

The ammoxidation of the starting cyclic compound by the fluidized bed reaction according to the present invention may be carried out with use of any type of fluidized bed reactors, which has desirably a multi-step cyclone separator built-in at the top, the lower end of the dip-leg of the first step cyclone being positioned at a level between the oxygen-containing gas inlet and the starting cyclic compound inlet. The preferred embodiment includes, for example, the one shown in FIG. 1. In this context, the present invention is not limited to the embodiment described specifically in FIG. 1.

In the fluidized bed reactor of FIG. 1 is charged a catalyst. The oxygen-containing gas is supplied from the gas inlet A through the supply pathway 2, and the carbocyclic compound or heterocyclic compound and ammonia are supplied from the gas inlet B provided at a part higher than the gas inlet A through the supply pathway 3 to the fluidized bed reactor 1, respectively. The catalyst particles involved in the gas flow are separated from the gas flow in a cyclone separator at the top of the reactor and returned to the bottom part of the catalyst layer. The reaction gas having the catalyst particles separated therefrom is exhausted from the fluidized bed reactor 1.

One of the features of the present invention resides in that the positions of supplying the starting cyclic compound and oxygen-containing gas, respectively, to the fluid catalyst bed are specified in relation to the amounts/weights of the fluid catalyst present in the upper area of the supplying positions/levels, respectively.

More particularly, in the aforementioned fluidized bed reactor 1, a reaction zone ranges from the oxygen-containing gas inlet to the inlet of the cyclone separator provided at the top of the reactor. If the ratio of the amount of catalyst fluidized at the area higher than the level of the inlet of the starting cyclic compound, Wb, to the amount of catalyst fluidized at the area higher than the level of the oxygen-containing gas inlet, Wa, is in a restricted and specified range, the nitrile as the objective product can be produced in a high yield. More particularly, when the ratio of Wb/Wa is in the range of 0.01–0.95, preferably 0.05–0.9, by weight, ammoxidation reaction can be carried out in a wide range of the concentration of the starting cyclic compound, and the nitrile can be obtained in a high selectivity in a high yield and stably with passage of time.

If the ratio Wb/Wa exceeds 0.95, the yield of and the selectivity to the nitrile tends to decrease, and the reaction rate and the selectivity would be significantly lowered with the passage of time. If the ratio Wb/Wa is less than 0.01 on the other hand, the reactor would be too large for the practical use due to the increased amount of the catalyst not actually used in the reaction zone.

The weights of the catalyst Wb and Wa are defined by the following equations:

$$Wb=(Pb-Po) \times S,$$

$$Wa=(Pa-Po) \times S,$$

wherein Pa represents the static pressure at the oxygen-containing gas inlet A, Pb represents the static pressure at the starting cyclic compound gas inlet B, Po represents the static pressure at the inlet of the cyclone and S represents the cross section of the fluidized bed.

Introduction of gases fed via the inlet A and the inlet B is desirably to be made so that gases are fed uniformly across the cross-section of a reactor, and it is thus required that the number and the location/arrangement of nozzles for feeding gases be selected with due consideration of this taken in mind. It is also desired that the velocity of gases leaving from nozzles be as uniform as possible across the cross-section of each of nozzles.

These requirements may be met when feeding pipes each with a nozzle of a selected diameter are arranged properly. The inlet A can comprise perforated plates.

Consideration on uniform introduction of gases into a fluidized bed reactor such as those referred to above is required in general in conventional fluidized bed operation or reaction, and also applies to the operation of the present invention as being important.

The gases to be supplied to a fluidized bed reactor in the present invention, which are basically three species, namely an oxygen-containing gas, a gas containing the starting cyclic compound, and ammonia, may be fed independently from each other or may be fed in admixture of at least two.

The concentration of the starting cyclic compound in the gas containing the starting cyclic compound may be in the range of 0.3 to 15 volume , preferably 0.5 to 10 volume %.

The molar ratio of ammonia to the starting cyclic compound may be in the range of 0.7 to 15, preferably 1.0 to 10, and the mole ratio of oxygen to the starting cyclic compound may be in the range of 1 to 40, preferably 2 to 30.

The ammonia can be of a commercial grade.

Air is a typical example of the oxygen-containing gas, but air can be enriched with oxygen or diluted with an adequate diluent such as nitrogen, steam or carbon dioxide. One of the advantages inherent in the present invention may be that the ammoxidation does not require a substantial presence of steam added.

Ammonia can be supplied separately from the starting cyclic compound. When the starting cyclic compound contains a formyl group, in particular, the starting cyclic compound should preferably be fed separately from ammonia. The ammonia inlet is not necessary at the same level as the inlet for the starting cyclic compound, but can be at a level higher or lower than the level of the inlet for the starting cyclic compound.

Ammonia can be fed so that it is partly in admixture with the oxygen-containing gas, and the starting cyclic compound can similarly be fed to fluidized bed reactor 1 in admixture with a part of the oxygen-containing gas.

The reaction temperature is in the range of 200–500° C., preferably 250–460° C. While the reaction pressure may be atmospheric, super-atmospheric or sub-atmospheric pressure, it is preferably in the range from atmospheric pressure to 2 kg/cm$^3$Gauge.

The contact time is in the range of 0.01–20 seconds, more particularly 0.05–10 seconds, more particularly 0.1–6 seconds, based on the gas volume at the reaction temperature and the reaction pressure. The contact time is obtained from the following equation:

$$\text{the contact time } \theta = Wb/(D \times Q)$$

wherein D represents an apparent bulk density of the catalyst, and Q represents a flow rate (volume) of a total gas, namely a gas volume supplied per unit time.

The catalyst used in the present invention is a metal oxide catalyst containing vanadium (referred to hereinafter as V)

and/or molybdenum (referred to hereinafter as Mo). It is preferably a metal oxide catalyst containing, in addition to V and/or Mo, at least one element selected from the group consisting of Li, Na, K, Cs, Mg, Ca, La, Ce, Ti, Zr, Nb, Ta, Cr, W, Mn, Re, Fe, Co, Ni, Cu, Ag, Zn, B, Al, Si, Ge, Sn, Pb, P, Sb, Bi and Te. More preferably, it is a metal oxide catalyst having a composition represented by the following experical formula:

$$Fe_aSb_bX_cQ_dR_eO_f(SiO_2)_g$$

wherein X represents V and/or Mo, Q represents at least one element selected from the group consisting of Li, Na, K, Cs, Mg, Ca, La, Ce, Ti, Zr, Nb, Ta, Cr, W, Mn, Re, Co, Ni, Cu, Ag, Zn, Al, Ge, Sn and Pb, R represents at least one element selected from the group consisting of P, B, Bi and Te, suffixes a, b, c, d, e, f and g represent atomic ratios, and are in the range of a=5–15, b=5–100 (preferably 10–60), c=0.01–12 (preferably 0.1–10), d=0–15, e=0–10, f=number corresponding to the oxides produced by bonding of each of the above described ingredients to oxygen, and g=10–200.

As the method for preparing the fluidized bed catalyst, any methods known in the art are used. The catalyst can be prepared for example by spray drying a slurry prepared from the ingredient raw materials with an appropriate means to form it into particles, which are then subjected to calcination. In particular, as the method for preparing a fluidized bed catalyst containing the aforementioned Fe, Sb, V and/or Mo as the essential ingredients, it is preferred to employ a method for preparing an aqueous slurry comprising a crystalline iron antimonate and vanadium component and/or molybdenum component, spray drying the slurry, and then calcining the dry product obtained (see Japanese Patent Laid-Open Publication No. 126548/1992).

The catalyst has a particle diameter in the range of about 10–500 $\mu$m, and the average particle diameter in the range of about 30–200 $\mu$m, preferably 40–100 $\mu$m. It has a bulk density in the range of 0.5–2 g/cm³, preferably 0.7–1.5 g/cm³.

The embodiments and advantages of the present invention are specifically described below with reference to examples, but the present invention is not limited to these examples.

The catalyst used in the ammoxidation reaction and the method for preparing it are described below.

[Catalyst A]

A fluidized bed catalyst having an empirical formula of $Fe_{10}Sb_{20}V_{4.5}Cr_4P_{0.3}Mo_{0.5}Mg_2Te_{0.5}O_{77.5}(SiO_2)_{50}$ was prepared as follows.

(I) Powder of antimony trioxide (1.75 kg) was provided.

(II) A mixture of nitric acid (sp. gr. 1.38, 2.6 liters) and demineralized water (3.2 liters) was warmed, and electrolytic iron powder (335 g) was added to the mixture.

(III) Silica sol (SiO₂, 20% by weight; 9.02 kg) was provided.

To (II) were added (III) and (I) in this sequence with stirring well, and the mixture was adjusted to pH 2 with 15% aqueous ammonia. The slurry was heated with stirring at 100° C. for 3 hours.

(IV) Phosphoric acid (content, 85%; 20.5 g) was provided.

(V) Chromium nitrate (961 g) was dissolved in demineralized water (3.0 liters).

(VI) Ammonium metavanadate (316 g) was added to demineralized water (2.0 liters) and heated, and oxalic acid (632 g) was added portionwise to form a solution.

(VII) Ammonium paramolybdate (52.7 g) was dissolved in demineralized water (350 ml).

(VIII) Magnesium nitrate (308 g) was dissolved in demineralized water (700 ml).

(IX) Telluric acid (68.8 g) was dissolved in demineralized water (1.0 liter).

To the slurry thus prepared were added (IV), (V), (VI), (VII), (VIII) and (IX), and the mixture was stirred amply. The slurry was spray dried with a rotary-disc spray dryer. Fine spherical particles thus obtained were calcined at 200° C. for 2 hours and 400° C. for 3 hours. Final calcination was carried out at 820° C. for 4 hours.

[Catalyst B]

A fluidized bed catalyst having an empirical formula of $Fe_{10}Sb_{15}V_4Cr_2La_{0.5}Al_1O_{60.25}(SiO_2)_{60}$ was prepared in the same manner as catalyst A except that the final calcination of the catalyst was carried out at 810° C. for 2 hours.

[Catalyst C]

A fluidized bed catalyst having an empirical formula of $Fe_{10}Sb_{13}V_{6.5}Mo_1W_{0.5}Ni_1O_{69.75}(SiO_2)_{55}$ was prepared in the same manner as catalyst A except that the final calcination of the catalyst was carried out at 800° C. for 3 hours.

[Catalyst D]

A fluidized bed catalyst having an empirical formula $V_{10}P_{10}Zn_1O_{53}(SiO_2)_{40}$ was prepared as follows.

To demineralized water (5.0 kg) was dissolved oxalic acid (1.44 kg) followed by vanadium pentoxide (813 g). After the oxalic acid and the oxide were completely dissolved, to the solution were added a solution of zinc nitrate (266.0 g) in demineralized water (500 g) and then 85.3% phosphoric acid (1.02 kg). The resulting solution was heated at 100° C. for 3 hours. After the heat treatment, silica sol (SiO₂: 20.4% by weight, 10.5 kg) was added, and the mixture was stirred amply. The slurry thus obtained was spray dried with a rotary-disc spray dryer. Fine spherical particles thus obtained were calcined at 250° C. for 4 hours. Final calcination was carried out at 760° C. for 2 hours.

[Catalyst E]

A fluidized bed catalyst having an empirical formula of $Mo_{15}Fe_{10}Ni_{0.5}K_{0.2}O_{60.6}(SiO_2)_{30}$ was prepared as follows.

After iron nitrate (4.82 kg) was dissolved in demineralized water (9.72 kg), silica sol (SiO₂: 20.4% by weight, 10.5 kg) was added. To this mixture were added a solution of nickel nitrate (175 g) and potassium nitrate (24.3 g) in demineralized water (750 g), followed by a solution of ammonium paramolybdate (3.14 kg) in demineralized water (18.7 kg). The resulting mixture was heated at 100° C. for 2 hours. The slurry thus obtained was spray dried with a rotary-disc spray dryer. Fine spherical particles obtained were calcined at 400° C. for 2 hours. Final calcination was carried out at 550° C. for 2 hours.

[Catalyst F]

A fluidized bed catalyst having an empirical formula of $Fe_{10}Sb_{17}V_3Cr_4P_{0.7}Mo_{0.5}K_{0.5}O_{66.0}(SiO_2)_{40}$ was prepared as follows.

(I) Powder of antimony trioxide (1.75 kg) was provided.

(II) A mixture of nitric acid (sp. gr. 1.38, 3.1 liters) and demineralized water (3.8 liters) was warmed, and electrolytic iron powder (394 g) was added to the mixture.

(III) Silica sol (SiO₂, 20% by weight; 8.50 kg) was provided.

To (II) were added (III) and (I) in this sequence with stirring well, and the mixture was adjusted to pH 2 with 15% aqueous ammonia. The slurry was heated with stirring at 100° C. for 3 hours.

(IV) Phosphoric acid (content, 85%; 56.8 g) was provided.

(V) Chromium nitrate (1.13 kg) was dissolved in demineralized water (3.5 liters).

(VI) Ammonium metavanadate (248 g) was added to demineralized water (1.7 liters) and heated, and oxalic acid (517 g) was added portionwise to form a solution.

(VII) Ammonium paramolybdate (62.0 g) was dissolved in demineralized water (400 ml).

(VIII) Potassium nitrate (35.3 g) was dissolved in demineralized water (100 ml).

To the slurry thus prepared were added (IV), (V), (VI), (VII) and (VIII), and the mixture was stirred amply. The slurry was spray dried with a rotary-disc spray dryer. Fine spherical particles thus obtained were calcined at 200° C. for 2 hours and 400° C. for 3 hours. Final calcination was carried out at 810° C. for 4 hours.

[Catalyst G]

A fluidized bed catalyst having an empirical formula of $Fe_{10}Sb_{20}V_7Cr_{0.5}P_{1.2}Cs_{0.2}O_{76.35}(SiO_2)_{60}$ was prepared in the same manner as catalyst A except that the final calcination of the catalyst was carried out at 810° C. for 4 hours.

[Catalyst H]

A fluidized bed catalyst having an empirical formula of $Fe_{10}Sb_{23}V_4Cr_{3.5}Cu_{0.5}Zn_1O_{77.75}(SiO_2)_{50}$ was prepared in the same manner as catalyst A except that the final calcination of the catalyst was carried out at 790° C. for 4 hours.

[Catalyst I]

A fluidized bed catalyst having an empirical formula $Mo_{15}Fe_8Co_1P_{0.5}O_{59.25}(SiO_2)_{30}$ was prepared as follows.

In demineralized water (7.78 kg) was dissolved iron nitrate (3.86 kg), and silica sol ($SiO_2$: 20.4%; 10.5 kg) was added to the solution. To the resulting mixture was added a solution of cobalt nitrate (350 g) in demineralized water (1 kg), followed by phosphoric acid (content, 85.3%; 68 g) and finally a solution of ammonium paramolybdate (3.14 kg) in demineralized water (18.7 liters). The resulting mixture was heated at 100° C. for 2 hours. The slurry thus obtained was spray dried with a rotary-disc spray dryer. Fine spherical particles thus obtained were calcined at 400° C. for 2 hours. Final calcination was carried out at 550° C. for 3 hours.

[Catalyst J]

A fluidized bed catalyst having an empirical formula of $V_{10}P_{10}Ni_{0.5}O_{50.5}(SiO_2)_{40}$ was prepared as follows.

To demineralized water (6 liters) was dissolved oxalic acid (1.8 kg), followed by vanadium pentoxide (1.01 kg). After the mixture formed a clear solution, a solution of nickel nitrate (161.6 g) in demineralized water (300 g) and then 85.3% phosphoric acid (1.28 kg) were added to the mixture. The resulting solution was heated at 100° C. for 3 hours. After heat treatment, silica sol ($SiO_2$: 20.4%, 13.1 kg) was added, and the mixture was stirred amply. The slurry thus obtained was spray dried with a rotary-disc spray dryer. Fine spherical particles thus obtained were calcined at 250° C. for 4 hours. Final calcination was carried out at 750° C. for 2 hours.

The activity was tested by the following method. A catalyst was charged in a fluidized bed reactor in which the catalyst fluidizing part has an internal diameter of 5 cm. To the reactor were supplied a starting cyclic compound, ammonia and air. The reaction pressure is an atmospheric pressure.

Conversion and yield were defined as follows:

$$\text{Conversion (\%)} = \frac{\text{Number of moles of the starting cyclic compound consumed in the reaction}}{\text{Number of moles of the starting cyclic compound supplied}} \times 100$$

$$\text{Yield (\%)} = \frac{\text{Number of moles of objective nitrile produced}}{\text{Number of moles of the starting cyclic compound supplied}} \times 100$$

EXAMPLES AND COMPARATIVE EXAMPLES

A vertical fluidized bed reactor as schematically shown in FIG. 1 was used.

Gases were supplied to the reactor under the conditions shown in Tables 1 and 3. The results are shown in Tables 2 and 4.

In Comparative Examples 1–10, except for Comparative Examples 3 and 10, all of the three starting gases are supplied from the inlet A, and thus Wa for the oxygen containing gas and Wb for the starting cyclic compound are the same. Thus, Wb/Wa equals 1.

TABLE 1

| Examples and Comparative Examples | Starting cyclic compound | Method for supplying starting gases and proportion thereof (% by volume) | | | | | |
|---|---|---|---|---|---|---|---|
| | | Inlet (A) | | | Inlet (B) | | |
| | | Air | Ammonia | Starting cyclic compound | Air | Ammonia | Starting cyclic compound |
| Example 1 | 2,6-dichloro-toluene | 85.0 | — | — | — | 10.0 | 5.0 |
| Comparative Example 1 | ditto | 85.0 | 10.5 | 5.0 | — | — | — |
| Example 2 | m-xylene | 60.0 | — | — | 5.0 | 30.0 | 5.0 |
| Comparative Example 2 | ditto | 65.0 | 30.0 | 5.0 | — | — | — |
| Example 3 | toluene | 79.0 | — | — | — | 15.0 | 6.0 |
| Comparative Example 3 | ditto | 79.0 | — | — | — | 15.0 | 6.0 |
| Example 4 | p-methoxytoluene | 86.0 | — | — | — | 12.0 | 2.0 |
| Comparative Example 4 | ditto | 86.0 | 12.0 | 2.0 | — | — | — |
| Example 5 | p-tolunitrile | 88.0 | — | — | — | 8.0 | 4.0 |
| Comparative Example 5 | ditto | 88.0 | 8.0 | 4.0 | — | — | — |

TABLE 2

| Examples and Comparative Examples | Catalyst | Wb/Wa | Contact period (second) | Reaction temperature (° C.) | Nitrile produced | After two hour reaction Conversion (%) | Yield (%) | After ten hour reaction Conversion (%) | Yield (%) |
|---|---|---|---|---|---|---|---|---|---|
| Example 1 | A | 0.80 | 5.5 | 360 | 2,6-dichloro-benzonitrile | 100 | 84.5 | 99.5 | 84.4 |
| Comparative Example 1 | A | 1.0 | 5.5 | 360 | ditto | 98.5 | 83.6 | 92.4 | 75.1 |
| Example 2 | B | 0.50 | 3.0 | 420 | isophthalo-nitrile | 99.6 | 84.2 | 96.5 | 83.9 |
| Comparative Example 2 | B | 1.0 | 3.0 | 420 | ditto | 99.5 | 84.0 | 91.8 | 79.1 |
| Example 3 | C | 0.65 | 2.5 | 440 | benzonitrile | 98.3 | 82.5 | 97.5 | 82.5 |
| Comparative Example 3 | C | 0.98 | 2.5 | 440 | ditto | 98.6 | 82.7 | 93.1 | 74.9 |
| Example 4 | D | 0.35 | 4.5 | 370 | p-methoxy-benzonitrile | 100 | 33.4 | 100 | 31.7 |
| Comparative Example 4 | D | 1.0 | 4.5 | 370 | ditto | 100 | 33.4 | 95.7 | 25.8 |
| Example 5 | E | 0.70 | 4.0 | 350 | terephthalo-nitrile | 100 | 95.1 | 98.6 | 94.2 |
| Comparative Example 5 | E | 1.0 | 4.0 | 350 | ditto | 100 | 94.8 | 90.3 | 81.1 |

TABLE 3

| Examples and Comparative Examples | Starting cyclic compound | Inlet (A) Air | Ammonia | Starting cyclic compound | Inlet (B) Air | Ammonia | Starting cyclic compound |
|---|---|---|---|---|---|---|---|
| Example 6 | 2,3-dimethyl-pyridine | 77.5 | — | — | — | 17.5 | 5.0 |
| Comparative Example 6 | ditto | 77.5 | 17.5 | 5.0 | — | — | — |
| Example 7 | 3-methylpyridine | 73.0 | — | — | — | 21.0 | 6.0 |
| Comparative Example 7 | ditto | 73.0 | 21.0 | 6.0 | — | — | — |
| Example 8 | 2-methylpyrazine | 70.0 | — | — | 5.0 | 20.0 | 5.0 |
| Comparative Example 8 | ditto | 75.0 | 20.0 | 5.0 | — | — | — |
| Example 9 | quinaldine | 79.7 | — | — | — | 15.8 | 4.5 |
| Comparative Example 9 | ditto | 79.7 | 15.8 | 4.5 | — | — | — |
| Example 10 | 2-thiophene carboaldehyde | 77.5 | — | — | — | 20.0 | 2.5 |
| Comparative Example 10 | ditto | 77.5 | — | — | — | 20.0 | 2.5 |

Method for supplying raw material gases and proportion thereof (% by volume)

TABLE 4

| Examples and Comparative Examples | Catalyst | Wb/Wa | Contact period (second) | Reaction temperature (° C.) | Nitrile produced | After two hour reaction Conversion (%) | Yield (%) | After ten hour reaction Conversion (%) | Yield (%) |
|---|---|---|---|---|---|---|---|---|---|
| Example 6 | F | 0.40 | 2.0 | 380 | 2-cyano-3-methylpyridine | 100 | 70.3 | 100 | 70.5 |
| Comparative Example 6 | F | 1.0 | 2.0 | 380 | ditto | 100 | 69.4 | 57.1 | 22.3 |
| Example 7 | G | 0.60 | 2.0 | 370 | 3-cyanopyridine | 100 | 86.9 | 99.5 | 87.0 |

TABLE 4-continued

| Examples and Comparative Examples | Catalyst | Wb/Wa | Contact period (second) | Reaction temperature (° C.) | Nitrile produced | After two hour reaction Conversion (%) | After two hour reaction Yield (%) | After ten hour reaction Conversion (%) | After ten hour reaction Yield (%) |
|---|---|---|---|---|---|---|---|---|---|
| Comparative Example 7 | G | 1.0 | 2.0 | 370 | ditto | 100 | 86.9 | 87.8 | 74.6 |
| Example 8 | H | 0.20 | 1.5 | 400 | 2-cyanopyrazine | 100 | 78.8 | 98.5 | 78.9 |
| Comparative Example 8 | H | 1.0 | 1.5 | 400 | ditto | 100 | 78.2 | 91.4 | 64.3 |
| Example 9 | I | 0.90 | 2.0 | 410 | 2-cyanoquinoline | 100 | 35.6 | 100 | 35.3 |
| Comparative Example 9 | I | 1.0 | 2.0 | 410 | ditto | 100 | 34.8 | 64.5 | 18.7 |
| Example 10 | J | 0.15 | 1.5 | 400 | 2-cyanothiophene | 99.8 | 91.5 | 97.9 | 92.1 |
| Comparative Example 10 | J | 0.98 | 1.5 | 400 | ditto | 99.7 | 91.6 | 78.3 | 67.4 |

What is claimed is:

1. In a process for preparing a heterocyclic nitrile comprising a member selected from the group consisting of cyanopyridine, cyanopyrazine, cyanoquinoline, cyanothiophene, cyanopiperidine, and a mixture thereof, the process comprising ammoxidating a starting cyclic compound comprising a corresponding N-containing or S-containing heterocyclic compound selected from the group consisting of pyridine, pyrazine, quinoline, thiophene and piperidine substituted by a member selected from the group consisting of methyl, ethyl, propyl, isopropyl, formyl, acetyl, hydroxymethyl, hydroxyethyl, hydroxyisopropyl, methoxycarbonyl, ethoxycarbonyl, propoxycarbonyl and isopropoxycarbonyl, in a reaction zone of a fluidized bed reactor in the presence of a metal oxide catalyst containing vanadium and/or molybdenum in a fluidized bed, the improvement which comprises forming the fluidized bed by supplying an oxygen-containing gas through an oxygen-containing gas inlet provided at the bottom of the fluidized bed reactor, and by supplying the starting cyclic compound and ammonia at a level higher than the oxygen-containing gas inlet so that the ratio of the amount of catalyst (Wb) fluidized at a level higher than an inlet of the starting cyclic compound to the amount of catalyst (Wa) fluidized at a level higher than the oxygen-containing gas inlet in the reaction zone is in the range of Wb/Wa of 0.05 to 0.9 by weight, and conducting the ammoxidation reaction for more than 10 hours.

2. A process according to claim 1, wherein a mixture of the starting cyclic compound and ammonia is supplied in a molar ratio of ammonia to the starting cyclic compound of 0.7 to 15 at a level higher than the oxygen-containing gas inlet.

3. A process according to claim 1, wherein the catalyst is a metal oxide fluidized bed catalyst comprising (1) vanadium and/or molybdenum, and (2) at least one of elements selected from the group consisting of K, Cs, Mg, La, Cr, W, Fe, Co, Ni, Cu, Zn, Al, Si, P, Sb and Te.

4. A process according to claim 1, wherein the catalyst is a metal oxide fluidized bed catalyst comprising iron, antimony and at least one member selected from the group consisting of vanadium and molybdenum as essential ingredients and silica as a support, and represented by an empirical formula:

$$Fe_aSb_bX_cQ_dR_eO_f(SiO_2)_g$$

wherein

X represents V and/or Mo,

Q represents at least one element selected from the group consisting of K, Cs, Mg, La, Cr, W, Co, Ni, Cu, Zn and Al, R represents at least one element selected from the group consisting of P, B, Bi and Te; and suffixes a, b, c, d, e, f and g represent atomic ratios, and are in the range of a=5–15, b=10–60, c=0.1–10, d=0–6, e=0–10, f=number corresponding to the oxides produced by bonding each of the above described ingredients to oxygen, and g=10–200.

5. A process according to claim 1, wherein ammoxidation is carried out without addition of steam.

* * * * *